(12) United States Patent
Xiang et al.

(10) Patent No.: US 6,653,319 B1
(45) Date of Patent: Nov. 25, 2003

(54) PHARMACEUTICAL FORMULATION FOR POORLY WATER SOLUBLE CAMPTOTHECIN ANALOGUES

(75) Inventors: Tian-Xiang Xiang, Lexington, KY (US); Bradley D. Anderson, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/216,883

(22) Filed: Aug. 12, 2002

Related U.S. Application Data

(60) Provisional application No. 60/311,570, filed on Aug. 10, 2001.

(51) Int. Cl.⁷ .................. A61K 31/4738; C07D 491/22
(52) U.S. Cl. .......................... 514/283; 546/14; 546/48
(58) Field of Search ............................ 514/283; 546/48, 546/14

(56) References Cited

U.S. PATENT DOCUMENTS

| | | |
|---|---|---|
| 4,399,282 A | 8/1983 | Miyasaka et al. |
| 4,727,064 A | 2/1988 | Pitha |
| 5,447,936 A | 9/1995 | Hausheer et al. |
| 5,468,754 A | 11/1995 | Hausheer et al. |
| 5,552,156 A | 9/1996 | Burke |
| 5,674,874 A | 10/1997 | Hausheer et al. |
| 5,736,156 A | 4/1998 | Burke |
| 5,958,937 A | 9/1999 | Hausheer et al. |
| 6,194,579 B1 | 2/2001 | Hausheer |

OTHER PUBLICATIONS

C Jaxel et al. Structure–activity study for the actions of camptothecin derivatives . . . pp. 1465–1469. Cancer Res, Vol 49, Issue 6 1989.
YH Hsiang et al. DNA topoisomerase I–mediated DNA cleavage and cytotoxicity of camptothecin . . . pp 3 4385–4389.Cancer Res., Vol 49, Issue 16 1989.
YH Hsiang et al. Arrest of replication forks by drug stabilized topoisomerase I–DNA clevable . . . pp. 5077–5082. Cancer Res., Vol 49, Issue 18 1989.
Robert P. Hertzberg et al. Modifications of the Hidroxy Lactone Ring of Camptothecin . . . pp. 715–720. American Chemical Soc. 1989.
Fassberg J. et al. A Kinetic and Mechanistic Study of the Hydrolysis of Camptothecin . . . pp. 676–682. Journal of Pharm. Sciences Vol 81, No. 7, Jul. 1992.
JG Supko et al. Pharmacokinetics of the 9–amino and 10,11–methylenedioxy derivatives . . . pp. 3062–3069. Cancer Res., Vol 53, Issue 13 1993.
NB Haas et al. Phase I/pharmacokinetic study of topotecan by 24–hour continuous . . . pp. 1220–1226.Cancer Res., Vol 54, Issue 5 1994.
Bom, David et al. The Novel Silatecan 7–tert–Butylmethilsilyl–10–hydroxy . . . pp. 3970–3980. 2000. American Chemical Society.

*Primary Examiner*—Charanjit S. Aulakh
*Assistant Examiner*—F. Patterson
(74) *Attorney, Agent, or Firm*—King & Schickli, PLLC

(57) ABSTRACT

The present invention provides a general method to retard the precipitation inception time for poorly water-soluble camptothecin analogues from a supersaturated solution by a chemical conversion approach via pH alteration. This method is successfully utilized to prepare stable parenteral formulations for silatecan 7-t-butyldimethylsilyl-10-hydroxycamptothecin (DB-67), a poorly water-soluble lipophilic camptothecin analogue, in aqueous solutions containing β-cyclodextrin sulfobutyl ether (SBE-CD) or other solubilizing agents. The formulations manufactured by this method are more simple and cost-effective, of higher doses and better quality in terms of manufacture loss and formulation stability, and can be free of organic solvents (e.g., DMSO or N-methyl-2-pyrrolidinone).

55 Claims, 6 Drawing Sheets

PHARMACEUTICAL FORMULATION FOR POORLY WATER SOLUBLE CAMPTOTHECIN ANALOGUES

This application claims the benefit of U.S. Provisional Patent Application Serial No. 60/311,570 filed Aug. 10, 2001.

This invention was made with Government support under NCI Contract N01-CM-77108. The Government may have certain rights in this invention.

TECHNICAL FIELD

The present invention relates to the field of compositions for treatment of a cancer in an animal. In particular, the present invention relates to a method for formulating an aqueous solution of a poorly water-soluble lipophilic camptothecin or camptothecin analog, and to compositions formulated thereby.

BACKGROUND OF THE INVENTION

Successful formulation of many new drug candidates in a parenteral or oral dosage form is often limited by low solubilities of these drugs in an aqueous solution and/or physical-and chemical instability over a relevant time period. In recent years, progress has been made in developing various solubilization formulation approaches, including salt formation, cosolvent, complexation, mixed micelles/liposomes, emulsions, and micro/nanoparticles. However, for some very poorly water-soluble drugs, solubilization approaches are not sufficient to achieve a desired dosage and a supersaturated solution of drugs stable during parenteral or oral administration may be one of few alternatives.

The inhibition of tumor cell growth by camptothecin analogues is believed to be linked to their action on DNA topoisomerases. Structure-activity studies show that successful inhibition of DNA topoisomerase I by camptothecin analogues requires an intact lactone ring (E-ring, species I in FIG. 1.) functionality. Camptothecin analogues having open lactone ring structures (carboxylate form), while quite soluble in water, are poorly accumulated by cancer cells, exhibit limited activity against the topoisomerase enzyme, and may be more toxic to healthy cells than the lactone form.

Unfortunately, the E-ring intact lipophilic camptothecin analogues have a very poor solubility in water. In the past, poor solubility has prevented the extensive use of highly lipophilic camptothecin analogues in clinical treatment of cancer even though lipophilic camptothecin analogues provide several important advantages over their water-soluble counterparts, such as relatively superior tissue penetration/retention, bioavailability, more consistently optimized dosage and schedule for administration, and less interpatient variability. Indeed, while a number of water soluble camptothecin derivatives including. Camptosar, topotecan, 9-amino-camptothecin, 7-(4-methylpiperazinomethylene)-10,11-methylenedioxy camptothecin, 10,11-methylenedioxy-camptothecin and 10,11-ethylenedioxy-camptothecin have either been on the market, studied preclinically, or used in clinical trials to treat certain types of human cancer, few clinical studies in human patients involving poorly water soluble, highly lipophilic camptothecin analogs [e.g., camptothecin, 10-hydroxy-7-ethyl camptothecin (SN38), and silatecan 7-t-butyldimethylsilyl-10-hydroxycamptothecin (DB-67)] have been conducted. This is largely attributed to the difficulty in developing pharmaceutical formulations that allow the direct administration of the poorly water-soluble, active camptothecin lactone species to human patients with cancer.

Silatecan 7-t-butyldimethylsilyl-10-hydroxycamptothecin (DB-67) is an experimental drug under consideration for clinical testing by the National Cancer Institute for cancer chemotherapy. As shown in FIG. 1, DB-67 is one of a class of A and B ring modified camptothecin analogs. Because of its increased lipophilicity and dual 7-alkylsilyl and 10-hydroxy substitution, DB-67 displays superior binding to cellular and liposomal membranes and enhanced drug stability in the presence of human serum albumin when compared with clinically relevant, more hydrophilic camptothecin analogues. In vitro cytotoxicity assays indicate that DB-67 is of comparable potency to other FDA approved camptothecin analogs (e.g., Camptosar and Hycamtin). A viable formulation for intravenous delivery of DB-67 should maintain a desired dose (1–3 mg/mL) exclusively in the lactone form and of optimal physical and chemical stability.

SUMMARY OF THE INVENTION

In accordance with the purposes of the present invention as described herein, a novel method for formulating an aqueous solution of a lipophilic camptothecin or camptothecin analog, and compositions formulated thereby, are provided. In one aspect, the present invention provides a method for preparing a stable supersaturated solution of a lipophilic camptothecin or a camptothecin analog, comprising formulating an alkaline solution of the lipophilic camptothecin or camptothecin analog, and acidifying the alkaline solution in the presence of a solubilizing agent. The alkaline solution may be formulated to have a pH of greater than about 10.0.

The alkaline camptothecin or camptothecin analog may be acidified by diluting into an acidic solution in the presence of a solubilizing agent to achieve a final pH of up to about 6.0. Desirably, the acidic solution may include a buffer suitable for maintaining a pH of said acidic solution at up to about 6.0, for example buffers selected from the group of buffers consisting of, but not limited to, citrate, acetate, lactate, or any mixture thereof.

The solubilizing agent may be selected from a group consisting of a cyclodextrin, a liposome, thermodynamically stable colloidal dispersions (e.g. micelles or microemulsions) containing surface-active agents, an emulsion, or any mixture thereof. Typically, the cyclodextrin solubilizing agent may be a water-soluble β-cyclodextrin derivative, selected from the group consisting of sulfobutyl ether β-cycllodextrin, 2-hydroxypropyl β-cyclodextrin, any other suitably chemically modified β-cyclodextrin, and any mixture thereof. When liposomes are selected as the solubilizing agent, typically they will be formulated as an acidic liposomal suspension having a pH of up to about 6.0. Suitable thermodynamically stable colloidal dispersions may be formulated to have a pH of up to about 6.0, and may comprise a mixture of a surfactant lipid such as Cremophor EL, Vitamin E TPGS, various Pluronics (e.g., polyethylene oxide/polypropylene oxide polymers, Tween 80), and the like. The dispersions may also contain a water miscible co-solvent selected from the group consisting of ethanol, polyethylene glycol (PEG), propylene glycol (PG), glycerol, or any mixture thereof. Dextrose or other suitable excipients may be added to adjust tonicity.

Typically, the lipophilic camptothecin or camptothecin analog may be camptothecin, silatecan 7-t-butyldimethylsilyl-10-hydroxycamptothecin, 10-hydroxy-7-ethyl camptothecin, 9-nitrocamptothecin, silatecan 7-t-butyldimethylsilyl-camptothecin, 7-methylcamptothecin, 7-ethylcamptothecin, 7-propylcamptothecin, 7-butylcamptothecin, or mixtures thereof.

In another aspect, a method for preparing a stable supersaturated solution of a lipophilic camptothecin or a camptothecin-analog is provided, comprising the steps of solubilizing the camptothecin or camptothecin analog of choice in an alkaline solution, and diluting the alkaline solution containing the solubilized camptothecin or camptothecin analog into an acidic solution in the presence of a solubilizing agent, selected from the solubilizing agents as described above. The properties of the alkaline and acidic solutions are as described above. The desired solubilizing agent may be added to the alkaline solution prior to diluting the-alkaline solution into the acidic solution, or may be dissolved into the acidic solution.

The alkaline solution may contain an amount of base (for example, sodium hydroxide) approximately double the concentration of lipophilic camptothecin or camptothecin analog. Typically, the acidic solution will contain an amount of strong acid, such as for example hydrochloric acid, sufficient to neutralize the alkaline solution containing camptothecin or camptothecin analog. Buffers may be included in the acidic solution as described above. Advantageously, the method as described provides a stable, supersaturated composition of lipophilic camptothecin or camptothecin analog which may be lyophilized for long-term storage without significant loss of drug activity upon reconstitution.

In yet another aspect of the present invention, a composition suitable for parenteral or oral administration for the treatment of a cancer in an animal is provided, comprising an aqueous solution containing a therapeutically sufficient amount of a lipophilic camptothecin or camptothecin analog formulated as described above and including the lipophilic camptothecin or camptothecin analog and a solubilizing agent. The lipophilic camptothecin or camptothecin analog may be included in the composition of the present invention in an amount of from about 0.5 to about 3 mg/mL of solution.

The cyclodextrin and/or liposome solubilizing agents may be included in the composition in an amount of from about 10% to about 40% (w/v). In the case where a thermodynamically stable colloidal dispersion (e.g. micelles or microemulsions) is used as the solubilizing agent, an aqueous solution comprising about 12.5% v/v of a polyethoxylated lipid such as Cremophor EL and 12.5% v/v ethanol may be included. In the case where a liposome is used as a solubilizing agent, an acidic liposomal suspension may be used, containing lipids selected from the group consisting of egg phospholipids, cholesterol, dimyristoylphosphatidylcholine, dimyristoylphosphatidylglycerol, or any other suitable lipids or mixtures thereof.

The compositions manufactured by the method of the present invention are advantageously more simple and cost-effective to manufacture, provide a therapeutically suitable dose of poorly water soluble camptothecin or camptothecin analog, are stable during storage, and may be formulated to be free of undesirable organic solvents (e.g., DMSO or N-methyl-2-pyrrolidinone). Advantageously, the compositions may be lyophilized for long-term storage without significant loss of drug activity upon reconstitution for parenteral or oral administration.

Other objects and applications of the present invention will become apparent to those skilled in this art from the following description wherein there is shown and described a preferred embodiment of this invention, simply by way of illustration of the modes currently best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

DESCRIPTION OF THE DRAWINGS

The accompanying drawing incorporated in and forming a part of the specification illustrates several aspects of the present invention and, together with the description, serves to explain the principles of the invention. In the drawing.

Figure 1:
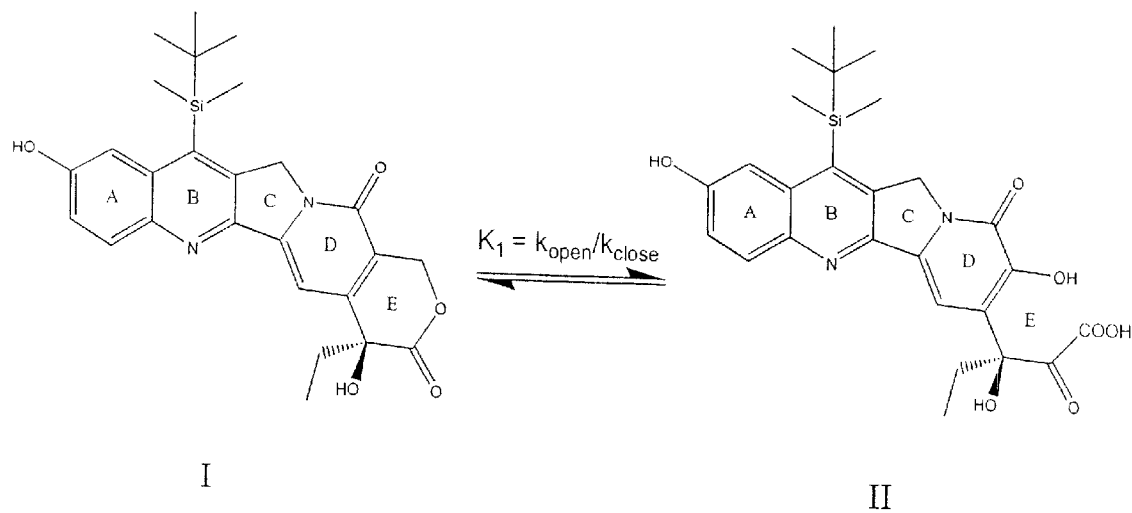
FIG. 1 shows the schematic structures of the lactone ring intact DB-67 (species I) and its E-ring opened counterpart (species II).

Reference will now be made in detail to the presently preferred embodiments of the invention, examples of which are illustrated in the accompanying drawing.

DETAILED DESCRIPTION OF THE INVENTION

As summarized above, the present invention relates to novel methods for formulating lipophilic camptothecins and camptothecin analogues, and to compositions formulated thereby. The methods and compositions of the present invention may be accomplished by various means which are illustrated in the examples below. These examples are intended to be illustrative only, as numerous modifications and variations will be apparent to those skilled in the art.

Our earlier studies have shown that precipitation occurs immediately during attempts to prepare a supersaturated solution by mechanically mixing a desired concentration (e.g., >1 mg/mL final concentration) of lactone-intact DB-67 drug in an organic solvent such as DMSO with a conventional dilution medium such as 20% (w/v) sulfobutyl ether β-cyclodextrin (SBE-CD). This may be attributed to the high local concentration of the drugs in their poorly water-soluble lactone form in the mixed solution. A proper control of the mixing pattern (local or uniform) and rate of addition of the drugs in their lactone form into the dilution medium has therefore been key to the success of this type of formulation approach. However, even with a controlled mixing pattern, formulation of a supersaturated lactone-intact DB-67 drug solution by simply adding a concentrated solution of the lactone into an aqueous solution, even in the presence of a suitable solubilizing agent, results in precipitation losses of the drug.

We then conceived that a supersaturated solution of a lipophilic camptothecin or camptothecin analog might be accomplished by employing a chemical approach, rather than a conventional mechanical approach. It has surprisingly been discovered that a uniform release of camptothecin and camptothecin analogs may be achieved by converting a lactone-ring opened camptothecin analog, which has a high solubility in water, to its lactone-ring closed counterpart, and that the rate of this chemical reaction can be regulated by controlling solution pH.

It has therefore been found possible to prepare clear stable aqueous solutions suitable for pharmaceutical administration, which would otherwise be subject to rapid precipitation if other mechanical methods had been employed. Using the method of the present invention, aqueous solutions containing therapeutically useful concentrations of 1–3 mg/mL camptothecin analogues and 10–40% (w/v) cyclodextrins may be achieved without drug precipitation. Typically, the aqueous solutions contain at least 2 mg/mL DB-67 and 20% (w/v) β-cyclodextrin derivatives such as SBE-CD or 2-hydroxypropyl β-cyclodextrin (HP-CD) as solubilizing agents.

Previously, liposomes have been utilized to prepare aqueous suspensions of pharmaceutically active camptothecins. However, the preparation procedure is usually complex involving many tedious steps during which drug loss (10–20%) is often found to occur. Such losses in drug concentration are especially difficult to control when the suspension is supersaturated with respect to the active component(s). Utilizing the present invention, the liposomal suspension can be prepared in the absence of camptothecin analogues, and then mixed with a basic camptothecin solution in one final step. Advantageously, this preparation method minimizes the loss of the active component(s) during the preparation process and provides a better control of formulation quality. Furthermore, since the initial liposomal suspension is free of camptothecin analogues, commercial sources of liposomes can be used to prepare the liposomal formulation, lowering the cost of the manufacture process. Utilizing the present method, we are successful in preparing stable liposomal solutions with negligible loss (<2%) of DB-67 during the preparation process.

Utilizing the present method, it is also possible to prepare stable solutions with other solubilizing agents such as a mixture of Cremophor EL and ethanol in water. Accordingly, it will be appreciated that the present method allows formulation of aqueous pharmaceutical preparations of poorly water-soluble camptothecin analogues using a variety of solubilizing agents.

The formulation of the present invention may include a pharmaceutically acceptable buffer to maintain an acidic pH such that the camptothecin analogues are preserved in the active lactone form. Typically, the pH range is maintained desirably below about 6.0, and may be regulated by any buffer suitable for pharmaceutical formulation. Such buffers include, but are not limited to, citrate, acetate, and lactate.

Another embodiment of this invention is the lyophilization of the prepared aqueous solution so that the mixing procedure described above is conducted by manufacturer rather than by physician before the administration to a cancer patient.

It will be appreciated by those of skill in the art that the present invention provides a simple, cost-effective, and safe method for formulating a therapeutically useful aqueous solution comprising a lipophilic camptothecin or camptothecin analog. Advantageously, the compositions formulated by the present method may be formulated to be free of organic solvents (e.g., DMSO or N-methyl-2-pyrrolidinone), in contrast to conventional methods requiring use of organic solvents to solubilize camptothecin.

EXAMPLES

Set forth in greater detail below are specific details related to selected modes for carrying out the methods and compositions of the present invention. The examples set forth herein are in no way intended to limit the scope of the invention. Those of skill in the art will realize that, given the teachings provided herein, many variations of the methods are possible that will fall within the scope of the present invention.

Example 1

A clear solution comprising a DB-67 concentration of 2 mg/mL in its lactone form and stable for at least three days was prepared as follows. DB-67 was accurately weighed (20 mg/mL) and added to a sodium hydroxide solution having a NaOH concentration twice that of the drug concentration. The suspension was placed on a shaker and incubated with shaking at 25° C. until the DB-67 was fully dissolved. It was then passed through a 0.2 μm filter to remove particulates.

An aliquot of this filtered DB-67 basic solution was then mixed with a 22.2% (w/v) SBE-CD acidic solution at a ratio of 1:9 (v/v). A sufficient amount of HCl was present in the final solution to neutralize the alkaline DB-67 solution. Citric acid (2 mM) was included to maintain the pH of the final solution below 4.5. The prepared solution was incubated for two hours until the chemical conversion was complete.

Example 2

Cyclodextrin/DB-67 solution was prepared as in Example 1, except that HP-CD was used instead of SBE-CD.

Example 3

A clear solution comprising a DB-67 concentration of 1 mg/mL in its lactone form and stable for at least three days was prepared as follows. The DB-67 basic solution was prepared as in Example 1.

An aliquot of the filtered DB-67 basic solution was mixed with an acidic EPL-Diluent liposomal suspension (NSC 704057) at a ratio of 1:19 (v/v). Immediately prior to mixing, a sufficient amount of HCl was added to the liposomal suspension to neutralize the alkaline DB-67 solution. Citric acid (2 mM) was also added to the liposomal suspension to maintain pH of the final solution at 4.4. The prepared solution was incubated for two hours until the chemical conversion was complete.

Example 4

A clear solution comprising a DB-67 concentration of 2 mg/mL in its lactone form and stable for at least three hours was prepared as follows. A solution containing DB-67 and NaOH was prepared as described in Example 1. An aliquot of the filtered solution was mixed with an acidic aqueous cosolvent solution containing 12.5% (v/v) Cremophor EL, 12.5% (v/v) ethanol, and 4% (w/v) dextrose at a DB-67: acidic aqueous cosolvent ratio of 1:9 (v/v). Immediately prior to mixing, a sufficient amount of HCl to neutralize the alkaline DB-67 solution was added. Citric acid (5 mM) was added also to the solution to maintain the pH of the final solution at 4.2. The prepared solution was incubated for two hours until the chemical conversion was complete.

Example 5

The final solution prepared as described in Example 1 was lyophilized in a glass vial and sealed with a rubber stopper and aluminum cap for long-term storage. The lyophilized preparation may be reconstituted with sterile water for administration orally or by a parenteral route to a cancer patient.

Example 6

Solubilities of DB-67 or camptothecin in a given solvent system were determined by adding an amount of the drugs well in excess of its estimated solubility to 1–2 mL of the desired solvent in a 4-mL glass vial. The capped vial was rotated in a VWR2010 incubator set at 25° C. for a period of 3–15 days. The sample was then passed through a 0.45 μm filter, except for liposome or emulsion samples, which were passed through a 1.2 μm filter. The collected sample was weighed, diluted with methanol, and analyzed by HPLC. The HPLC system consisted of a Discovery $C_{18}$ 15 cm×4.6 mm column and a Discovery $C_{18}$ 2 cm×4.6 mm 5 μm guard column (Supelco), a Beckman 110B solvent delivery module, a Rheodyne M7125 injector with a 20 μm injection loop (Rainin), a Waters M2487 Dual λ Absorbance detector set at 254 nm, an HP 3392A integrator, and a mobile phase of 25% and 41% (v/v) acetonitrile in 2% (w/v) triethylamine acetate for camptothecin and DB-67, respectively.

The solubility results for DB-67 in various solvent systems are summarized in Table 1. The solubility-pH profile for DB-67 in aqueous solution is presented in FIG. 2, where the curve is a non-least-squares fit using an equilibrium model for the base-catalyzed lactone-ring opening and ionization of substituents in DB-67 (10-OH and the —COOH when the lactone-ring is opened at a basic pH). As noted, the solubility of DB-67 in an aqueous solution of acidic pH (5.2), where DB-67 exists mostly in E-ring intact form, is 0.11 μg/mL, well below the target dosage of 2 mg/mL to maintain an appropriate administration time and volume. Various solubilization approaches such as cosolvents, complexation with water-soluble cyclodextrins (e.g., SBE-CD and HP-CD), emulsions, and liposomes failed to accomplish the desired dosage for DB-67 of 1–2 mg/mL.

Figure 2:
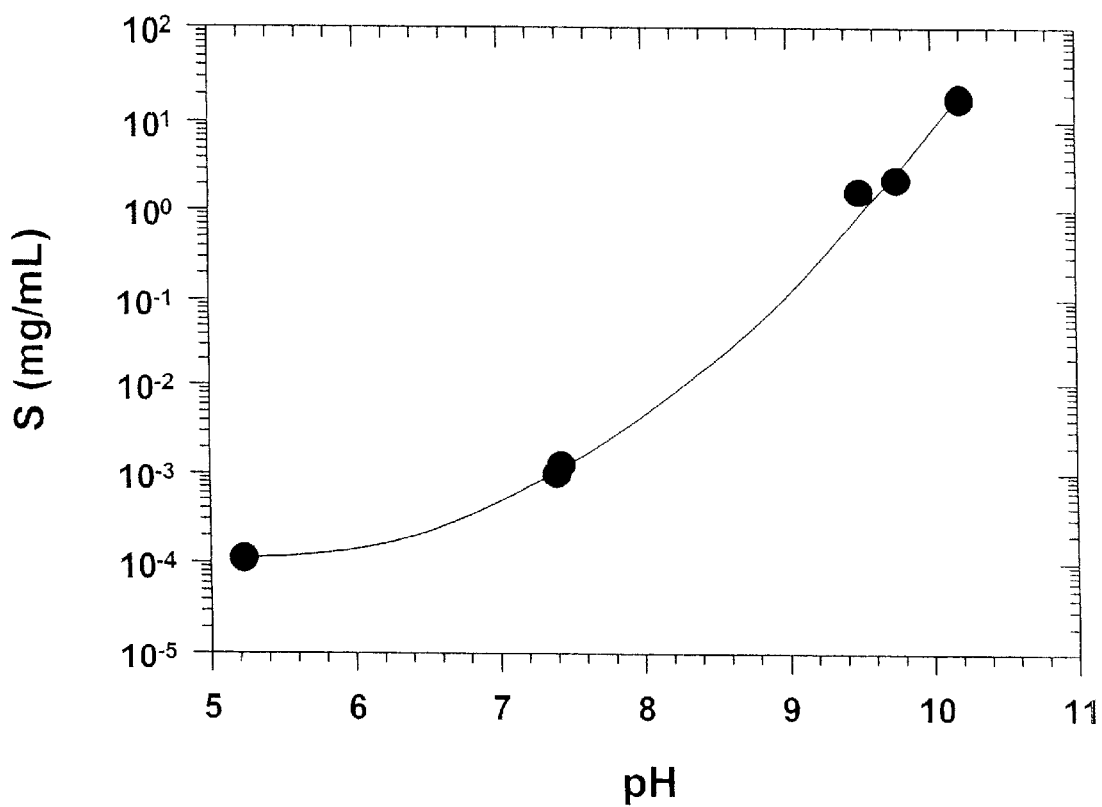
FIG. 2 shows the dependence of solubility S (mg/mL) for DB-67 in aqueous solution at 25° C. on solution pH value.

As also shown in Table 1 and FIG. 2, a solubility of ~18 mg/mL can be accomplished in an aqueous solution of pH >10.2. However, as noted above the ionized (alkaline) DB-67 exists mostly in the lactone-ring opened (carboxylated) form. Previous studies on other camptothecin analogues indicate that the lactone-ring opened species of a camptothecin analogue is therapeutically inactive, has a significantly shorter plasma half life, and exhibits greater toxicity than the lactone-ring intact species. This is supported by pharmacologic evidence from clinical studies in humans and other mammalian species receiving sodium camptothecin, 9-amino camptothecin and Topotecan.

Desirably, the present invention allows formulation of supersaturated pharmaceutical formulations with the required dosage for the lactone-ring intact DB-67 which are stable with respect to precipitation within an appropriate time period of administration (e.g., <24 hours).

TABLE 1

Solubilities of DB-67 in various solvent systems at 25° C.[a]

| Solvent | S (mg/mL) |
| --- | --- |
| Water/30 mM acetate buffer at pH 5.23 | $(1.11 \pm 0.00) \times 10^{-5}$ |
| Water/0.5 M carbonate buffer at pH 10.20 | $1.78 \times 10^{-1}$ |
| 40% (w/v) HPCD/water | $(4.9 \pm 0.2) \times 10^{-1}$ |
| 40% (w/v) SBE-CD/water/1 mM HCl | $(2.09 \pm 0.04) \times 10^{-1}$ |
| 40% PG, 10% (v/v) EtOH/water | $(1.73 \pm 0.04) \times 10^{-1}$ |
| 10% (v/v) PEG-400/water | $(3.3 \pm 0.5) \times 10^{-2}$ |
| 50% (v/v) PEG-400/water | $(2.0 \pm 0.3) \times 10^{-1}$ |
| Emulsion (20% soybean oil, 2% glycerin, 73% water, 4% Tween80, 1% eggPC) | $(2.06 \pm 0.05) \times 10^{-1}$ |
| Liposome (70:25:5 (mole) DMPC:Chol:DMPG) | $(7.4 \pm 0.3) \times 10^{-3}$ |
| 50% Cremophor, 50% (v/v) EtOH (Diluent-12) | $(7.5 \pm 0.2) \times 10^{0}$ |
| 5% Cremophor, 5% (v/v) in 5% (w/v) Dextrose/Water | $2.00 \times 10^{-1}$ |

[a]mean ± standard deviation from duplicate samples except in 10% (v/v) diluent-12 in 5% (w/v) dextrose/water and water/0.5 M carbonate buffer at pH 10.20 (single).

The results summarized in Table 1 indicate that DB-67 can be substantially solubilized in the presence ofβ-cyclodextrins (e.g., SBE-CD and HP-CD). Cyclodextrins are cyclic oligosaccharides with a hydrophobic cavity in the center. The most common cyclodextrins are α-, β, γ-cyclodextrins, consisting of 6, 7, and 8 α-1,4-linked glucose units, respectively. With recent development of manufacturing technology, water-soluble cyclodextrin derivatives formed, by alkylation or hydroxyalkylation of the primary hydroxyl groups in cyclodextrins have become less expensive, and are widely used in solubilization and stabilization of various drug agents because of their capability to form inclusion complexes with drug molecules having size compatible with the dimensions of the cyclodextrin cavity. As a second characterization step, the solubilization mechanisms for selected β-cyclodextrins (SBE-CD and HP-CD) are investigated, as described below (Example 7).

Example 7

Figure 3:
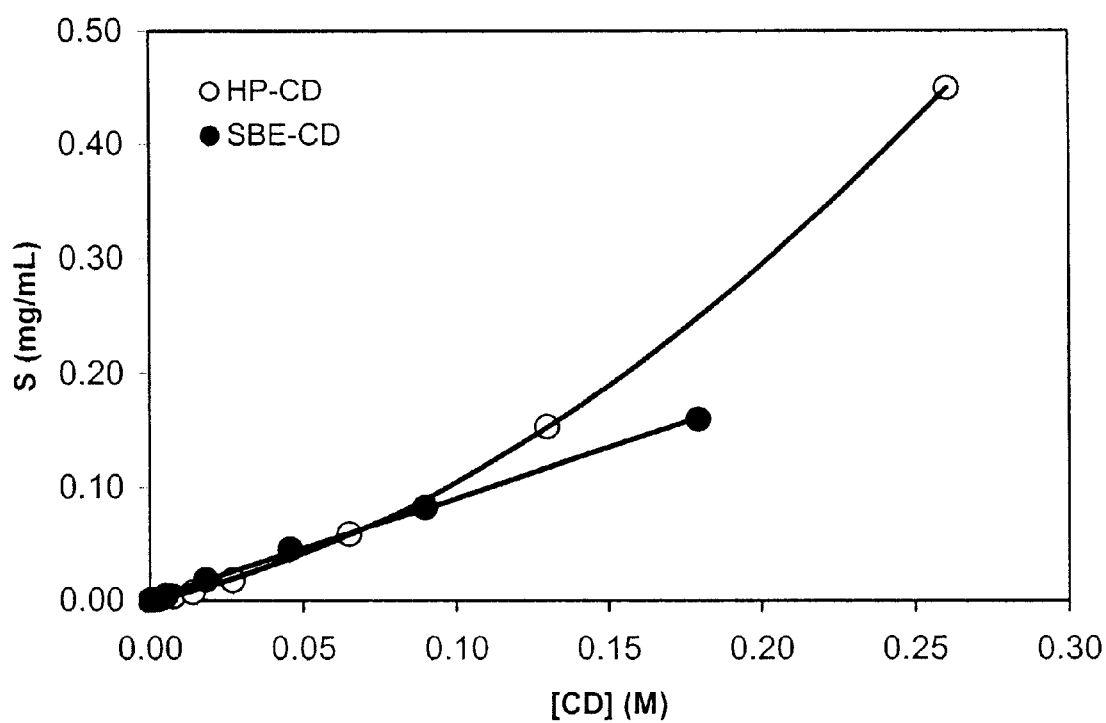
FIG. 3 shows the variation of solubility for the neutral E-ring closed DB-67 at 25° C. as a function of cyclodextrin concentrations (SBE-CD and HP-CD) in aqueous solution.

To understand the complexation mechanisms behind this solubilization effect, a solubility method was employed to determine the formation constant between a camptothecin analogue and a cyclodextrin derivative. In the solubility experiment, the solution pH was controlled below 4.6 with a 30 mM citrate buffer. As shown in FIG. 3, the linear solubility profile for DB-67 complexation with SBE-CD indicates a predominant formation of 1:1 complexation between the neutral E-ring closed DB-67 and SBE-CD. In contrast, a quadratic dependence of DB-67 solubility on cyclodextrin concentration was observed for complexation of the E-ring closed DB-67 with HP-CD, suggesting more 1:2 complexes at a higher HP-CD concentration.

In the limit of $[CD] >> S_o$, the relevant formation constants can be expressed as:

$$S = S_o(1 + K_f^{1:1}[CD] + K_f^{1:2}[CD]^2) \quad (1)$$

where $S_o$ is the solubility in the absence of cyclodextrins, $K_f^{1:1}$ and $K_f^{1:2}$ are the 1:1 and 1:2 complex formation constants, and [CD] is concentration of cyclodextrin. A linear least-squares fit of the data for SBE-CD as shown in FIG. 3 yields the complex formation constant of $K_f^{1:1}=$ $8.5\pm0.2\times10^3 M^{-1}(r^2=0.999)$. The linear behavior also suggests that only 1:1 complexes between the neutral E-ring intact DB-67 and SBE-CD are favorable. The inability for SBE-CD to form 1:2 complexes with DB-67 apparently arises from the presence of an average of seven negatively charged sulfobutyl ether groups in a SBE-CD molecule preventing the approach of two SBE-CDs to each other to form 1:2 complexes. A least-squares fit of the data for HP-CD as shown in FIG. 3 according to Equation 1 yields the 1:1 and 1:2 complex formation constants of $K_f^{1:1}= 5.8\pm0.2\times10^3 M^{-1}$ and $K_f^{1:1}=3.8\pm0.2\times10^4 M^{-1}(r^2=1.000)$. The ability of HP-CD to form 1:2 complexes with the E-ring intact DB-67 suggests that there, are at least two binding sites in the E-ring intact DB-67.

One of the key discoveries in the present invention is the utility of the hydrolysis reaction between the lactone-closed and lactone-opened species (I and II in FIG. 1) to slowly and uniformly release lactone-closed camptothecins in a dilution medium in order to prevent the precipitation of the active camptothecin analogues and maintain the physical stability of the formulation. Furthermore, cyclodextrins can not only solubilize camptothecin analogues in water but also potentially slow down the E-ring opening hydrolysis reaction in vivo increasing the lifetime of the drugs in human blood. Thus, it is necessary to investigate the hydrolysis kinetics of camptothecin analogues in solution.

Example 8

The reaction kinetics for the E-ring opened and closed DB-67 were investigated in aqueous solutions at pH 7.4 and 4.0, respectively. The reactions were thermostated at $25\pm0.1°$ C. by a circulation water bath and initiated by adding 0.1 mL of reactants (Species I DB-67 in DMSO or Species II DB-67 in 2 mM NaOH; see FIG. 1) to a 30 mM phosphate or acetate buffer solution with an initial reactant concentration of $2-4\times10^{-6}$ M. After the addition and at different time intervals, aliquots of the reaction solutions were withdrawn and immediately assayed by HPLC. The concentrations of both species I and II were monitored in order to evaluate the mass balance and other possible degradation products. Simultaneous non-linear least-squares fits of the kinetic profiles yield the first-order rate constants for the lactone-ring opening and closing processes of $k_{open}= 1.1\pm0.1\times10^{-4}$ s$^{-1}$ and $k_{close}=3.3\pm0.3\times10^{-4}$ s$^{-1}$. The mass balance results indicate that no other reaction processes contribute significantly to the variation of concentrations for species I and II DB-67.

We have also investigated the hydrolysis processes for the lactone-ring intact DB-67 (Species I) at pH 7.4 in the presence of 20% (w/v) SBE-CD and HP-CD, respectively. The temporal profiles for the disappearance of species I and the appearance of species II were found to follow the first-order kinetic models similar to those in the absence of cyclodextrins. The fitted rate constants are $k_{open}=(7.1\pm0.1)\times 10^{-5}s^{-1}$ and $k_{open}=(6.2\pm0.1)\times10^{-5}s^{-1}$ for 20% (w/v) SBE-CD and HP-CD, respectively. As noted above, the presence of 20% (w/v) SBE-CD or HP-CD reduces the rate for the lactone-ring opening process by 1.6- and 1.8-fold, respectively. The rate reduction is therefore more marked in the presence of HP-CD.

The mechanisms responsible for the improved stability of the therapeutically viable DB-67 may therefore be different for use of the solubilizing agents SBE-CD and HP-CD. In the case of 20% (w/v) HP-CD, more than 99.9% of DB-67 are included in the CD hydrophobic cavity, among which roughly 46% of the complexes are in the form of 1:2 complexes. If the hydrolysis site on the E-ring is included in the CD cavity in the 1:2 complexes with HP-CD but not in the 1:1 complexes, the E-rings in only about 46% DB-67 are protected from the attack by OH$^-$ ions. While not wishing to be bound by any particular theory, this may explain the approximately 44% reduction in the observed rate constant. On the other hand, in the presence of 20% (w/v) SBE-CD, more than 99.8% of DB-67 are bound to SBE-CD forming the predominantly 1:1 complexes. Although there perhaps are a small fraction of 1:1 complexes where the hydrolysis site on the lactone-ring is included in the CD cavity, the presence of the negatively charged sulfobutyl ether groups in SBE-CD may repel the surrounding OH$^-$ ions and reduce the rate for OH$^-$ catalyzed hydrolysis reaction.

The significantly reduced rate of hydrolysis to the carboxylate form in the presence of β-cyclodextrin derivatives suggests an additional benefit of the cyclodextrin formulations revealed in this invention. The stability of camptothecin analogues in their active lactone form in vivo may accordingly also increase the half-life of the drugs in human blood, potentially improving bioavailability and therapeutic usefulness.

Example 9

A successful pharmaceutical formulation with a supersaturated drug concentration requires a physical stability with respect to drug precipitation. In our first attempt, 20–25 mg/mL of DB-67 was loaded in DMSO because of the drug's high solubility in this solvent. The dissolved DB-67 was then added slowly to a 20% (w/v) SBE-CD aqueous solution by a volume ratio of 1:9 to achieve a final drug concentration of 2 mg/mL. The dilution rate was maintained at 0.10 mL/min. It was found that the precipitation occurred even during the mixing process and continued after the finish of mixing. Since, DB-67 exists in the lactone-ring intact form in DMSO, which has a very low solubility in water, the local drug concentration near the mixing region is so large that it is difficult to prevent the drugs from undergoing fast nucleation and precipitation. A proper control of the release pattern (local or uniform) and rate of DB-67 into the dilution medium is therefore critical to the success of this type of formulation approach.

As described above, a slow and uniform release of DB-67 into a dilution medium may be accomplished by employing a chemical approach, namely by converting the E-ring opened DB-67 (Species II, see FIG. 1), which is highly water-soluble, to the neutral E-ring closed DB-67 (Species I) in a controlled fashion. Studies on other camptothecin analogs suggest that the rate of this chemical reaction can be regulated by solution pH. Accordingly, 20 mg/mL of DB-67 was loaded in a sodium hydroxide solution with NaOH concentration maintained at twice that of the drug concentration. The prepared DB-67 alkaline aqueous solution was passed through a 0.2 μm filter before it was added slowly (0.11 mL/min) into 20% (w/v) acidic SBE-CD solution by a volume ratio of 1:9. In order to completely neutralize DB-67, HCl was present in the dilution solution in an amount equal to the amount of NaOH in the DB-67 alkaline solution. A small amount of acetate buffer (5 mM) was also included in the dilution medium to control the solution pH to about 4 in order to facilitate a timely conversion from the E-ring opened DB-67 to its E-ring closed counterpart.

Figure 4:
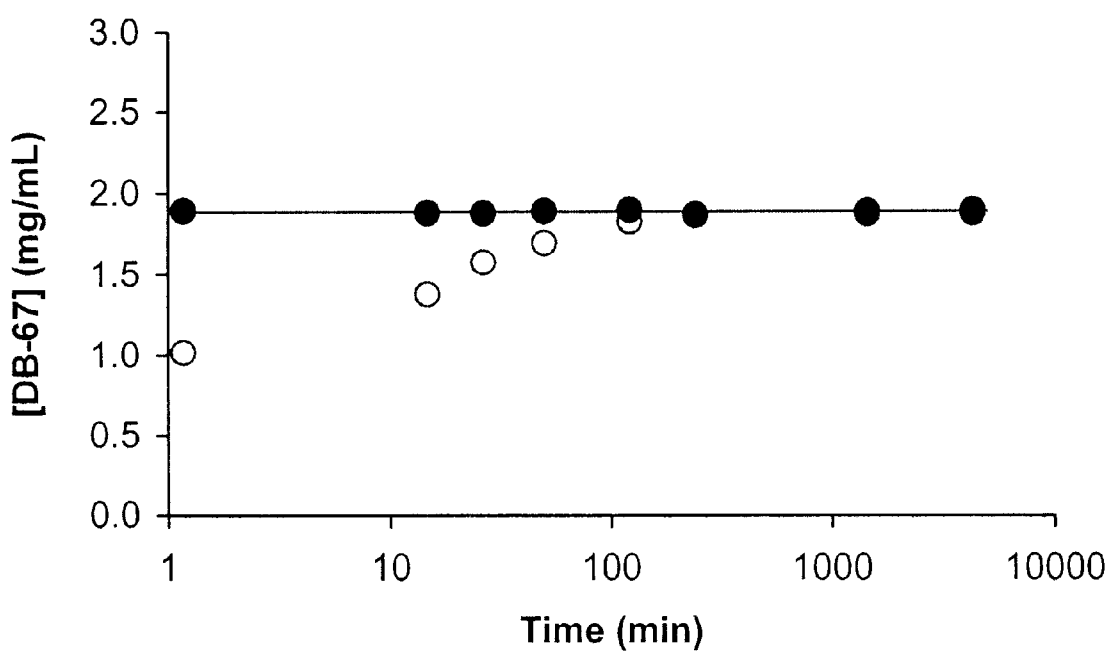
FIG. 4 shows the variations of DB-67 concentrations for the neutral E-ring closed DB-67 (open circles) and overall DB-67 concentrations (solid circles) in the supernatant after 1:9 dilution from an alkaline aqueous solution into 22% (w/v) SBE-CD as a function of time after mixing.

FIG. 4 shows the overall DB-67 concentration and the concentration of converted lactone-intact DB-67 in the solution at different time intervals. Overall DB-67 concentration remained constant over an extended period of three days, exceeding the target stability time of less than one day. At the measured solution pH of 4.4, the E-ring closed DB-67 slowly built up in the final solution in a uniform manner and the process was nearly complete within 100 minutes. This slow and uniform build-up of the lactone-ring intact DB-67 may explain the superior stability of this formulation approach in comparison with the simple mechanical method using DMSO as a solubilizing agent.

Example 10

Figure 5:
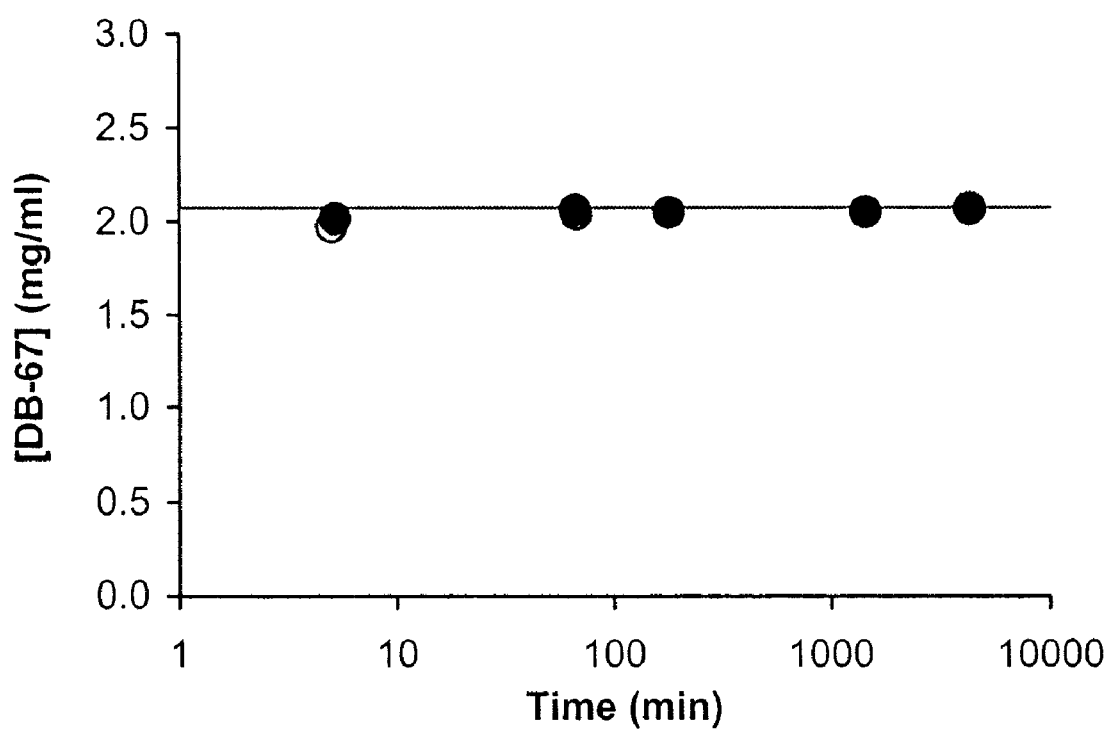
FIG. 5 shows the DB-67 concentrations in the filtered solutions of duplicate samples after reconstitution of the lyophilized formulation. The horizontal line indicates the averaged overall DB-67 concentration in the unfiltered solutions.

For long-term storage, the final solution containing 20% (w/v) SBE-CD and about 2 mg/mL lactone-ring intact DB-67 prepared according to the procedure described above was lyophilized after the chemical conversion process was nearly completed (>90%). Shortly after the lyophilization, the lyophilized sample was reconstituted and the stability of the reconstituted solution was examined following the same procedure as described above. The results are presented in FIG. 5. The reconstituted solution was stable for about seven days, suggesting that no significant occurrence of nucleation/precipitation during the lyophilization process and within about seven days after reconstitution.

Example 11

Figure 6:
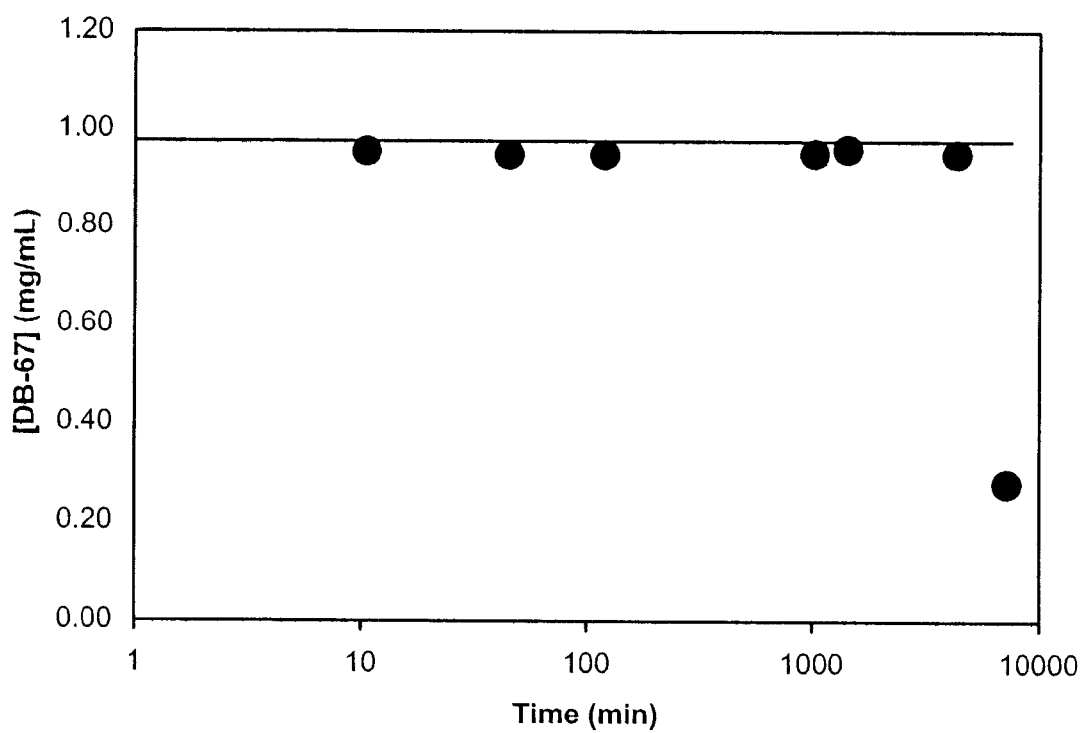
FIG. 6 shows the variations of DB-67 concentrations for the overall DB-67 concentrations in the supernatant after 1:9 dilution from an alkaline aqueous solution into an acidic liposomal suspension (NCS 754057; provided by the National Cancer Institute and manufactured by Ben Venue Laboratories, Inc., Bedford, Ohio 44146) as a function of time after mixing. The horizontal line is the overall DB-67 concentration in the sample.
Figure 7:
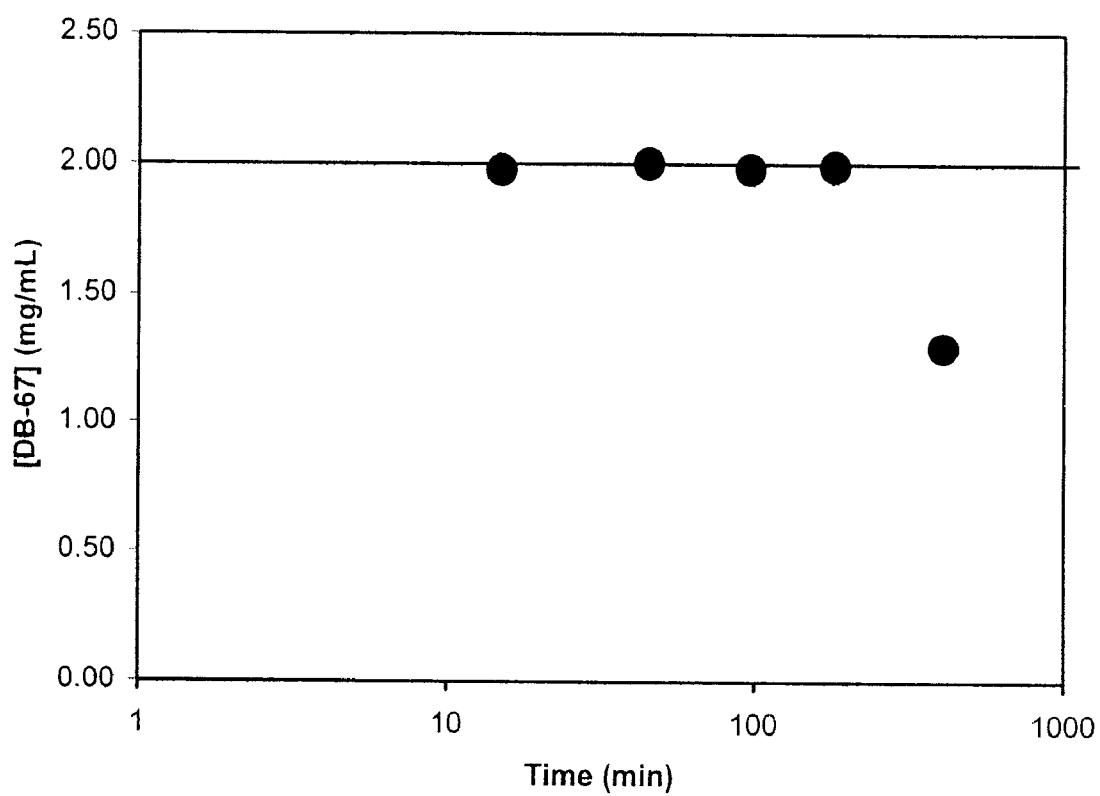
FIG. 7 shows the variations of DB-67 concentrations for the overall DB-67 concentrations in the supernatant after 1:9 dilution from an alkaline aqueous solution into acidic solution containing 12.5% (v/v) Cremophor EL, 12.5% (v/v) ethanol, and 4% (w/v) dextrose in water as a function of time after mixing. The horizontal line is the overall DB-67 concentration in the sample.

The precipitation profiles of DB-67 solutions containing other solubilizing agents such as liposomes and an acidic aqueous cosolvent solution comprising an equal volume mixture of ethanol and cremophor, prepared as described in Examples 3 and 4, respectively, were evaluated. The stability profiles are presented in FIGS. 6 and 7. The liposome/DB-67 solutions were stable for more than three days (FIG. 6). The acidic aqueous cosolvent/DB-67 solutions were stable for more than three hours. Dynamic light scattering measurements indicated that the average particle size in the acidic liposomal suspensions (pH 2.1 and 4.6) remained in a narrow range of 74–79 nm during five days' incubation, suggesting that the acidic liposomal suspension is stable for at least five days (FIG. 6).

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for preparing a stable supersaturated aqueous solution of a lipophilic camptothecin or a camptothecin analog, comprising formulating an alkaline solution of said lipophilic camptothecin or camptothecin analog, and acidifying said alkaline solution in the presence of a solubilizing agent.

2. The method of claim 1, wherein said alkaline solution is formulated to have a pH of at least 10.0.

3. The method of claim 1, wherein said alkaline camptothecin or camptothecin analog is acidified by diluting said alkaline solution into an acidic solution in the presence of a solubilizing agent to achieve a final pH of up to about 6.0.

4. The method of claim 3, wherein said acidic solution includes a buffer suitable for maintaining a pH of said acidic solution at up to about 6.0.

5. The method of claim 4, wherein said buffer is selected from the group of buffers consisting of citrate, acetate, lactate, and any mixture thereof.

6. The method of claim 1, wherein said solubilizing agent is selected from the group consisting of a cyclodextrin, a liposome, a thermodynamically stable colloidal dispersion, an emulsion, and any mixture thereof.

7. The method of claim 6, wherein said cyclodextrin is a water-soluble β-cyclodextrin derivative.

8. The method of claim 7, wherein said water-soluble β-cyclodextrin derivative is selected from the group consisting of sulfobutyl ether β-cyclodextrin, 2-hydroxypropyl β-cyclodextrin, and any mixture thereof.

9. The method of claim 6, wherein said liposome is formulated as an acidic liposomal suspension having a pH of up to about 6.0.

10. The method of claim 6, wherein said thermodynamically stable colloidal dispersion is formulated to have a pH of up to about 6.0.

11. The method of claim 10, wherein said thermodynamically stable colloidal dispersion comprises a surfactant lipid.

12. The method of claim 11, wherein said surfactant lipid is selected from the group consisting of Cremophor, Vitamin E TGPS, polyethylene oxide/polypropylene oxide polymers, Tween 80, and any mixture thereof.

13. The method of claim 11, wherein said thermodynamically stable colloidal dispersion includes a water miscible co-solvent selected from the group consisting of ethanol, polyethylene glycol, polypropylene glycol, glycerol, and any mixture thereof.

14. The method of claim 11, wherein said thermodynamically stable colloidal dispersion includes an agent for adjusting tonicity selected from the group consisting of dextrose, sodium chloride, and any mixture thereof.

15. The method of claim 1, wherein said lipophilic camptothecin or camptothecin analog is selected from the group consisting of camptothecin, silatecan 7-t-butyldimethylsilyl-10-hydroxycamptothecin, 10-hydroxy-7-ethyl camptothecin, 9-nitrocamptothecin, silatecan 7-t-butyldimethylsilyl camptothecin, 7-methylcamptothecin, 7-ethylcamptothecin, 7-propylcamptothecin, 7-butylcamptothecin, and any mixture thereof.

16. A method for preparing a stable supersaturated aqueous solution of a lipophilic camptothecin or a camptothecin analog, comprising the steps of:
    solubilizing said camptothecin or camptothecin analog in an alkaline solution; and
    diluting said alkaline solution containing said solubilized camptothecin or camptothecin analog into an acidic solution in the presence of a solubilizing agent.

17. The method of claim 16, wherein said solubilizing agent is added to said alkaline solution of camptothecin or camptothecin analog prior to diluting the alkaline solution into the acidic solution.

18. The method of claim 16, wherein said alkaline solution has a pH of at least about 10.0.

19. The method of claim 16, wherein said alkaline solution is diluted into said acidic solution to achieve a final pH of up to about 6.0.

20. The method of claim 16, wherein said acidic solution includes a buffer suitable for maintaining a final pH in said acidic solution of up to about 6.0.

21. The method of claim 20, wherein said buffer is selected from the group of buffers consisting of citrate, acetate, lactate, and any mixture thereof.

22. The method of claim 16, wherein said solubilizing agent is selected from the group consisting of a cyclodextrin, a liposome, a thermodynamically stable colloidal dispersion, an emulsion, and any mixture thereof.

23. The method of claim 22, wherein said cyclodextrin is a water-soluble β-cyclodextrin derivative.

24. The method of claim 23, wherein said water-soluble β-cyclodextrin derivative is selected from the group consisting of sulfobutyl ether β-cyclodextrin, 2-hydroxypropyl β-cyclodextrin, and any mixture thereof.

25. The method of claim 22, wherein said liposome is formulated as an acidic liposomal suspension having a pH of up to about 6.0.

26. The method of claim 22, wherein said thermodynamically stable colloidal dispersion is formulated to have a pH of up to about 6.0.

27. The method of claim 26, wherein said thermodynamically stable colloidal dispersion comprises a surfactant lipid.

28. The method of claim 27, wherein said surfactant lipid is selected from the group consisting of Cremophor, Vitamin E TGPS, polyethylene oxide/polypropylene oxide polymers, Tween 80, and any mixture thereof.

29. The method of claim 26, wherein said thermodynamically stable colloidal dispersion includes a water miscible co-solvent selected from the group consisting of ethanol, polyethylene glycol, polypropylene glycol, glycerol, and any mixture thereof.

30. The method of claim 26, wherein said thermodynamically stable colloidal dispersion includes an agent for adjusting tonicity selected from the group consisting of dextrose, sodium chloride, and any mixture thereof.

31. The method of claim 16, wherein said lipophilic camptothecin or camptothecin analog is selected from the group consisting of camptothecin, silatecan 7-t-butyldimethylsilyl-10-hydroxycamptothecin, 10-hydroxy-7-ethyl camptothecin, 9-nitrocamptothecin, silatecan 7-t-butyldimethylsilyl camptothecin, 7-methylcamptothecin, 7-ethylcamptothecin, 7-propylcamptothecin, 7-butylcamptothecin, and any mixture thereof.

32. The method of claim 16, further including the step of lyophilizing the stable, supersaturated solution for storage.

33. A composition for the treatment of a cancer in an animal, comprising an aqueous solution containing a therapeutically sufficient amount of a lipophilic camptothecin or camptothecin analog formulated by the steps of solubilizing said camptothecin or camptothecin analog in an alkaline solution, and diluting said alkaline solution into an acidic solution in the presence of a solubilizing agent.

34. The composition of claim 33, wherein said lipophilic camptothecin or camptothecin analog is selected from the group consisting of camptothecin, silatecan 7-t-butyldimethylsilyl-10-hydroxycamptothecin, 10-hydroxy-7-ethyl camptothecin, 9-nitrocamptothecin, silatecan 7-t-butyldimethylsilyl camptothecin, 7-methylcamptothecin, 7-ethylcamptothecin, 7-propylcamptothecin, 7-butylcamptothecin, and any mixture thereof.

35. The composition of claim 33, wherein said solubilizing agent is selected from the group consisting of a cyclodextrin, a liposome, a thermodynamically stable colloidal dispersion, an emulsion, and any mixture thereof.

36. The composition of claim 35, wherein said cyclodextrin is a water soluble β-cyclodextrin derivative.

37. The composition of claim 36, wherein said water soluble β-cyclodextrin derivative is selected from the group consisting of sulfobutyl ether β-cyclodextrin, 2-hydroxypropyl β-cyclodextrin, and any mixture thereof.

38. The composition of claim 35, wherein said liposome is formulated as an acidic.liposomal suspension having a pH of up to about 6.0.

39. The composition of claim 35, wherein said thermodynamically stable colloidal dispersion is formulated to have a pH of up to about 6.0.

40. The composition of claim 39, wherein said thermodynamically stable colloidal dispersion comprises a surfactant lipid.

41. The composition of claim 40, wherein said surfactant lipid is selected from the group consisting of Cremophor, Vitamin E TGPS, polyethylene oxide/polypropylene oxide polymers, Tween 80, and any mixture thereof.

42. The composition of claim 39, wherein said thermodynamically stable colloidal dispersion includes a water miscible co-solvent selected from the group consisting of ethanol, polyethylene glycol, polypropylene glycol, glycerol, and any mixture thereof.

43. The composition of claim 39, wherein said thermodynamically stable colloidal dispersion includes an agent for adjusting tonicity selected from the group consisting of dextrose, sodium chloride, and any mixture thereof.

44. The composition of claim 33, wherein said lipophilic camptothecin or camptothecin analog is included in an amount of from about 0.5 to about 3 mg/mL of solution.

45. The composition of claim 35, wherein said cyclodextrin solubilizing agent is included in an amount of from about 10% to about 40% w/v.

46. The composition of claim 35, wherein said liposome solubilizing agent is included in an amount of from about 10% to about 40% w/v.

47. The composition of claim 35, wherein said thermodynamically stable colloidal dispersion comprises-an aqueous solution of about 12.5% v/v Cremophor EL and 12.5% v/v ethanol.

48. The composition of claim 34, wherein said camptothecin analogue is silatecan 7-t-butyldimethylsilyl-10-hydroxycamptothecin.

49. The composition of claim 38, wherein said acidic liposomal suspension includes lipids selected from the group consisting of egg phospholipids, cholesterol, dimyristoylphosphatidylcholine, dimyristoylphosphatidylglycerol, and any mixture thereof.

50. The composition of claim 33, wherein said acidic solution comprises an amount of an acid suitable for neutralizing said alkaline camptothecin or camptothecin analog solution.

51. The composition of claim 50, wherein said acid is selected from the group consisting of hydrochloric acid, phosphoric acid, carbonic acid, formic acid, acetic acid, lactic acid, citric acid, and any mixture thereof.

52. The composition of claim 33, wherein said alkaline solution includes an amount of base double the amount of camptothecin or camptothecin analog.

53. The composition of claim 52, wherein said base is selected from the group consisting of sodium hydroxide, potassium hydroxide, sodium carbonate, and any mixture thereof.

54. The composition of claim 33, wherein said acidic solution includes a-buffer suitable for maintaining a pH of the acidic solution at up to about 6.0.

55. The composition of claim 54, wherein said buffer is selected from the group of buffers consisting of citrate, acetate, lactate, and any mixture thereof.

* * * * *